US006906044B2

(12) United States Patent (10) Patent No.: US 6,906,044 B2
Hermida Ochoa (45) Date of Patent: Jun. 14, 2005

(54) REGENERATION OF ARTICULAR CARTILAGE DAMAGED BY GRADE I AND II OSTEOARTHRITIS BY MEANS OF THE INTRAARTICULAR APPLICATION OF A MIXTURE OF SODIUM HYALURONATE AND CHONDROITIN SULFATE IN A GEL VEHICLE

(75) Inventor: Elias Humberto Hermida Ochoa, Colonia Roma (MX)

(73) Assignee: Alcon, Inc., Hunenberg (CH)

( * ) Notice: Subject to any disclaimer, the term of this patent is extended or adjusted under 35 U.S.C. 154(b) by 0 days.

(21) Appl. No.: 10/082,743

(22) Filed: Feb. 22, 2002

(65) Prior Publication Data

US 2004/0214793 A1 Oct. 28, 2004

(30) Foreign Application Priority Data

Nov. 13, 2001 (MX) .............................. PA/a/2001/011542

(51) Int. Cl.$^7$ ..................... A61K 31/737; A61K 31/728
(52) U.S. Cl. ........................................ 514/54; 536/55.1
(58) Field of Search ................... 514/54, 825; 536/55.1

(56) References Cited

U.S. PATENT DOCUMENTS

| | | |
|---|---|---|
| 4,486,416 A | 12/1984 | Soll et al. |
| 4,636,524 A | 1/1987 | Balazs et al. |
| 4,713,448 A | 12/1987 | Balazs et al. |
| 4,801,619 A * | 1/1989 | Lindblad .................... 514/825 |
| 5,099,013 A | 3/1992 | Balazs et al. |
| 5,143,724 A | 9/1992 | Leshchiner et al. |
| 5,409,904 A | 4/1995 | Hecht et al. |
| 5,498,606 A | 3/1996 | Soll et al. |
| 5,929,050 A | 7/1999 | Petito |
| 2002/0068718 A1 * | 6/2002 | Pierce .......................... 514/54 |

FOREIGN PATENT DOCUMENTS

| | | | |
|---|---|---|---|
| EP | 704216 | * 4/1996 | ......... A61K/31/725 |
| EP | 0 875 248 A1 | 11/1998 | |
| WO | WO 96/32929 | 10/1996 | |
| WO | WO 00/44367 | 8/2000 | |

OTHER PUBLICATIONS

Brown et al., "Gelatin/Chondroitin 6-Sulftae Microspheres for the Delivery of Therapeutic Proteins to the Joints," *Arthritis & Rheumatism*, 41(12):2185–2195 (Dec. 1998).
Buckwalter et al., "The Increasing Need for Nonoperative Treatment of Patients with Osteoarthritis," *Clinical Orthopaedics and Related Research*, 385:36–45 (2001).

Hardingham, "Chondroitin Sulfate and Joint Disease," *Osteoarthritis and Cartilage*, 6 (Suppl A): 3–5 (1998).
Nerucci et al., "Effects of chondroitin sulfate and interleukin–1β on human chondrocyte cultures exposed to pressurization: a biochemical and morphological study," *Osteoarthritis and Cartilage* 8:279–287 (2000).
Watanabe et al., "Roles of Aggrecan, a Large Chondroitin Sulfate Proteoglycan, in Cartilage Structure and Function," *J. Biochem* 124:687–693 (1998).
Dr. Elias Hermida Ochoa et al., "Treatment of Osteochondral Lesions with Intraarticular Application of a Mixture of Hyaluronate and Sodium Chondroitin Sulfate", May 2000.
Mark E. Adams, Guest Editor, "Viscosupplementation: A Treatment for Osteoarthritis", An International Symposium, Ottawa, ON, Canada, Sep. 11, 1992, Introduction, The Journal of Rheumatology 1993, vol. 20, Supplement 39, p. 2.
Endre A. Balazs et al., "Viscosupplementation: A New Concept in the Treatment of Osteoarthritis", The Journal of Rheumatology 1993, vol. 20, Supplement 39, pp. 3–9.
Jacques G. Peyron, "Intraarticular Hyaluronan Injections in the Treatment of Osteoarthritis: State–of–the–Art Review", The Journal of Rheumatology 1993, vol. 20, Supplement 39, pp. 10–15.
Mark E. Adams, "An Analysis of Clinical Studies of the Use of Crosslinked Hyaluronan, Hylan, in the Treatment of Osteoarthritis", The Journal of Rheumatology 1993, vol. 20, Supplement 39, pp. 16–18.
Jean–Pierre Pelletier et al., "The Pathophysiology of Osteoarthritis and the Implication of the Use of Hyaluronan and Hylan as Therapeutic Agents in Viscosupplementation", The Journal of Rheumatology 1993, vol. 20, Supplement 39, pp. 19–24.
Vladimir Bobic, MD, "Autologous Chondrocyte Transplantation", American Academy of Orthopaedic Surgeons Annual Meeting, Day 2–Mar. 16, 2000, pp. 1–6.
Joseph A. Buckwalter, MD, et al., "Restoration of Injured or Degenerated Articular Cartilage", Journal of the American Academy of Orthopaedic Surgeons, vol. 2, No. 4, Jul./Aug. 1994, pp. 192–201.

* cited by examiner

*Primary Examiner*—James O. Wilson
*Assistant Examiner*—Ganapathy Krishnan
(74) *Attorney, Agent, or Firm*—Barry L. Copeland

(57) ABSTRACT

Methods of treating osteochondral lesions by the intraarticular application of a mixture of sodium hyaluronate and chondroitin sulfate are disclosed.

5 Claims, 15 Drawing Sheets

REGENERATION OF ARTICULAR CARTILAGE DAMAGED BY GRADE I AND II OSTEOARTHRITIS BY MEANS OF THE INTRAARTICULAR APPLICATION OF A MIXTURE OF SODIUM HYALURONATE AND CHONDROITIN SULFATE IN A GEL VEHICLE

FIELD OF THE INVENTION

This invention is related to the treatment of osteochondral lesions by means of the intraarticular application of a mixture of hyaluronate and sodium chondroitin sulfate.

Specifically, this discovery has its application in the regeneration of the articular cartilage damaged by grade I and grade II osteoarthritis of the knee, shoulder, sacroiliac, hip, ankle, elbow, interphalangeal and wrist joints through the intraarticular application of a mixture of sodium hyaluronate and chondroitin sulfate in gel.

The main objective of the invention is to introduce the new medical use of the mixture of sodium hyaluronate and sodium chondroitin sulfate for the regeneration of damaged articular cartilage caused during osteoarthritis, treatment methods and the provision of the components for such therapies as well as the protection of such cartilage.

BACKGROUND OP THE INVENTION

Osteoarthritis is a condition that affects many millions of persons in the world for which to date there has been no effective treatment to resolve the complaint definitively and directly on the chondral lesion.

This disease consists of the gradual degeneration and destruction of the articular cartilage due to traumas and structural deformities of the joints and overweight. This process thins the cartilage through a phenomenon called apoptosis, or programmed cell death. When the surface area has disappeared due to the thinning, there is a grade I osteoarthritis; when the tangential surface area has disappeared, there is a grade two osteoarthritis. There are other levels of degeneration and destruction, which affect the deep and the calcified layers that border with the subchondral bone.

The clinical manifestations of the development of the condition are: increased volume of the joint, pain, crepitation and functional disability that, gradually and steadily, first hinders the performance of lengthy walks and forced flexion and extension movements, depending on the affected joint, and then pain and limitation of minimum efforts emerge as well as pain at rest which interrupts sleeping. If the condition persists without correction and/or therapy, the joint is totally destroyed, leading the patient to major replacement surgery with total prosthesis, or to disability.

Therapeutic methods for the correction of the articular cartilage lesions that appear during the osteoarthritic disease have been developed, but so far none of them have been able to achieve the regeneration of articular cartilage in situ and in vivo.

Among the methods we find the following:
a) The application of tendinous, periosteal, fascial, muscular or perichondral grafts.
b) The implantation of fibrin or cultured chondrocytes. (Osteochondral Grafts Improve Symptoms but May Increase Risks Of Osteoarthritis. medscape.com/con/2000/AAOS/story.cfm).
c) The administration of chondrogenic stimulating factors such as "insulin-like growth factors I and TGF-B".
d) Implantation of synthetic matrices, such as collagen, carbon fiber.
e) Others, such as electromagnetic fields. (J. Buckwalter, M. D., Van C. Mow, Ph. D. and Anthony Ratcliffe, Ph.D. Journal of the American Academy of Orthopaedic Surgery 1994; 2:192–202).

All of these have reported minimal and incomplete results with formation of repair, but not regenerative tissue, resulting in a poor quality tissue that can neither support the weighted load nor allow the restoration of an articular function with normal movement.

The treatment that has 74% to 90% effectiveness and produces excellent results, similar to that presented in this invention, is the transplantation of cultured autologous chondrocytes, a treatment started in 1987 in Sweden and in 1995 in the USA. It consists of taking chondral cellular material from the patient, sending it to a laboratory where it is seeded in a proper medium for its proliferation, and, once enough volume is achieved after a variable period that may last from weeks to months, transporting it in a special container and implanting it in the damaged tissues to cover the tissue's defects. This is an expensive procedure that requires the patient to be in the operating room for the removal of the necessary cellular material, and subsequently for the implantation of the proliferated material. Furthermore, a waiting period is needed for the implant to be ready. (VLADIMIR, Bobic, MD AAOS Annual Meeting, Mar. 16, 2000.)

A recent treatment, currently in vogue, is the intraarticular instillation of Hylan G-F 20 (Synvisc, Hyalgan, Artz etc.), a modified form of one of the substances contained in the product used in this invention. This substance only acts on the rheologism of the synovial fluid, producing an almost immediate sensation of free movement and a marked reduction of pain: however, its effect is temporary because that element remains within the articular chamber for only 72 hours before it is absorbed and metabolized. The residual effects of this substance act on the synovial receptors causing a pain reduction that lasts several weeks and even months. However, this isolated effect is counterproductive for the course of the disease and for the viability of the cartilage because, as it masks the symptoms, the joint is used with more intensity and its destruction is accelerated as the original problem is not corrected and the the damaged articular cartilage is not restored.

As an antecedent to this invention, in 1982, the applicant began applying sodium hyaluronate (SH) to thoroughbred race horses in his stable at Hipódromo de las Américas (Las Américas Race Track), in Mexico City, because the knees and ankles are the most commonly injured joints in these horses. Veterinarians at racetracks in the USA had already used this procedure, observing the beneficial reaction that this compound produced in the injured knees of the horses. The applicant considered its use in humans, with the addition of some substance to cause the restoration of the damaged surface.

The applicant observed that chondroitin sulfate (Cs), the most important part of the Agreecan molecule, lengthy chains bound to the core-protein, which are the basis of chondral support, might have a repaving effect.

In 1996 while visiting Alcon Laboratories in Mexico City, the applicant found out that one of the company's ophthalmologic products contained both above mentioned substances in a gel suspension (VISCOAT). The inventor obtained detailed information, including the product monograph that states that it has no reported side effects in intraocular use; furthermore, there are ample references from efficacy and safety studies of this product (CILCO, In, Summary of safety and efficacy for Viscoat, 1984). It was then that the applicant decided to use it in patients with osteoarthritis disorders of all degrees, and subsequently perform an analysis.

The above mentioned usual treatments include antiinflammtatories, antirheumatics, systemics, physiotherapy, infiltration of depot steroids and, recently, viscoprotection has emerged. It includes substances such as high molecular weight hyaluronic acid (Hylan G F 20) which is instilled in the joint and reduces the painful symptoms.

It has been proven that the change of the intraarticular fluids produces a blockage of the nociceptors of subsynovial and capsular tissues and that, in addition to the mechanical factors of the osteochondral pathology, the fluids exert a relevant influence with their lubricating properties. Thus the change in viscosity of these fluids acts favorably on the painful osteochondral symptoms when sodium hyaluronate is instilled.

Recent studies of a 5 year follow-up with these substances indicate that the clinical improvement is important and that it represents a remission factor of painful symptoms at short and medium term. However, adverse effects, characterized by severe pain, important synovial effusion, rash and ankle edema, have been reported in at least 7.2% of the treated patients.

This study reveals another alternative in the management of osteochondral lesions of the knee through the intraarticular application of the mixture of sodium hyaluronate and sodium chondroitin sulfate, based on the principles of chondrogenesis and viscoelasticity by implanting an artificial matrix that represents an indispensable repair factor, as in it the cloned chondrocytes can proliferate and restore the solution of continuity, regenerating the destroyed cartilage with the same original characteristics.

With this matrix, the symptomatic evolution is significantly favorable and long lasting due to the regeneration of chondral lesions and no side effects have been reported except in a patient who reported pain and a slight increase in Volume at the site of application, which subsided spontaneously in 24 hours; he was only given acetaminophen as an analgesic.

It must be pointed out that the product is applied exactly as it is presented for intraocular use and no change has been made in the formulation. A change in presentation with a larger capacity syringe is now being proposed, as the current presentation has 0.5 c.c. and 0.75 c.c. syringes.

It must also be pointed out that although this is the same preparation as that used intraocularly, its use for this purpose is totally different as it is applied in a conventional intraarticular manner as an inductor of chondrogenesis, to regenerate the cartilage destroyed by osteoarthritis.

As previously mentioned, experimental application of the compound in humans started in 1996, and excellent results noted. These were confirmed later by arthroscopy studies (direct view of the articular cartilage through the insertion of a camera into the joint), pathologic anatomy and histophysiologic studies, all of them consistent with the clinical findings that the regeneration of normal articular cartilage was achieved. This is why this treatment is presented as the only currently available procedure that can offer up to 95% regeneration of articular cartilage damaged by grade I and II osteoarthritis in any joint of the human body.

SUMMARY OF THE INVENTION

This invention was developed to solve the technique problem related to the treatment of the articular cartilage damaged by osteoarthritis.

This invention introduces a method to achieve regeneration of the articular cartilage by chondrogenic induction through the intraarticular implantation of an artificial matrix in patients with grade I or II osteoarthritis in any joint of the human body.

The regeneration process is elicited by implanting an artificial matrix formed by chondroitin sulfate where is the cloned chondrocytes are settled, where they mature and, in groups of 3 or 4, they form their own definitive hyaline matrix, duplicating the same pattern of the natural cartilage whereby the continuity of the articular surface is recovered, mobility is regained, pain is eliminated and thus function is recovered.

DESCRIPTION OF THE DRAWINGS

FIGS. 1 and 2 represent pre- and two years posttreatment arthroscopic images.

FIG. 3 represents the regeneration of the articular cartilage with De Novo cartilage.

FIGS. 4 and 5 are microscopic images that show the maturing of the zone tangential to the superficial layer where fully developed and maturing chondrocytes are found, surrounded by a hyaline matrix.

FIG. 6 is a histophysiological confirmatory image with the application of S-100 protein. It shows the reaction of the cartilaginous tissue to this test, which resulted positive.

Characteristics of the Product

Figure 1:
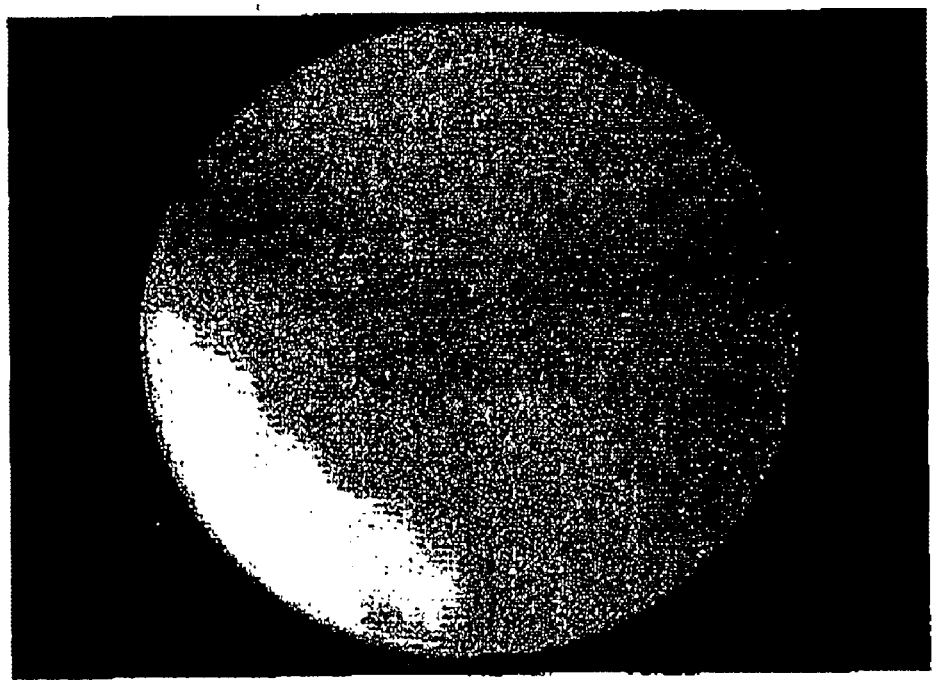
FIGS. 1 to 6 represent pre- and postimplantation arthroscopy images also shown as tests performed to patients who underwent the treatment: macro and microscopic confirmation of regeneration of the articular surface with De Novo cartilage with the same characteristics as the original, a conclusive pathology report and histophysiology tests (S-100 Protein) that confirm the characteristics of the regenerated cartilage.
Figure 2:
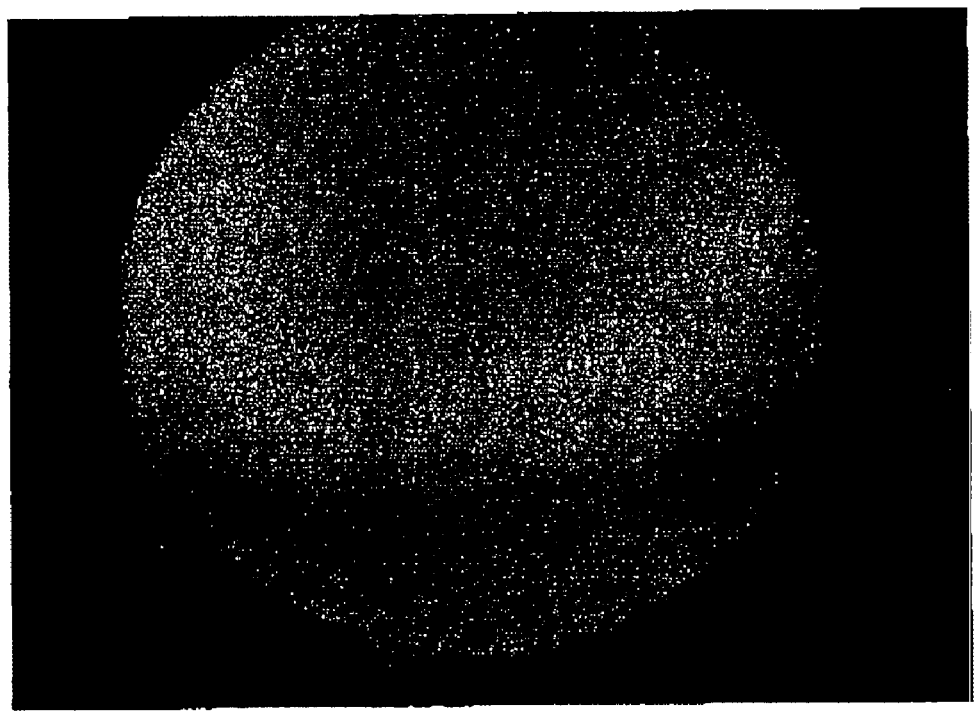

It is presented under the trade name of VISCOAT®, it is prescribed for the treatment of chondral lesions in Osteoarthritis (OA) in patients who fail to respond adequately to traditional non-drug therapies and to plain analgesics.

It is protected under U.S. Pat. No. 4,486,416 and it is also registered before the SSA (Mexican Health Secretariat) under registration number Reg SSA Mex. No. 0735 C 88.

This product has a gel presentation that contains a mixture of sodium hyaluronate and chondroitin sulfate; these substances exist in natural form in the human body as part of cartilage, synovial membrane, umbilical cord and vitreous humor of the eye.

Each cubic centimeter of the mixture contains 40 mg of chondroitin sulfate, 30 mg of sodium hyaluronate, 0.45 mg of sodium monobasic monohydrate phosphate, 2 mg of sodium dibasic anhydrous phosphate, 4.3 mg of sodium chloride and water.

DETAILED DESCRIPTION OF THE INVENTION

The product is applied by conventional intraarticular means with prior asepsis and antisepsis of the region. This is done in the treatment room of the physician's office; the product applied is called implant. As previously explained, CS is the most important part of Agreecan, it acts with its long chains inserted in the protein nucleus as a support element of the chondral stroma; it is thus that it serves as an artificial matrix that sticks to the bed of the lesion, allowing the cloned, unattached, peripheral chondrocytes of the erosion to settle in it and, when they mature, the chondrocytes secrete a definitive hyaline matrix that replaces the temporary one ("wet nurse") and thus it regenerates until it manages to recover the original shape and thickness. This has been verified when, upon performing control arthroscopy post-implant application, cartilage regeneration is observed macroscopically. Microscopically, findings of "De Novo" articular cartilage with normal morphological characteristics, as well as positive histophysiological results to S-100 protein, are reported.

The preferred method for this invention's chondrogenic induction is the intraarticular application of a mixture containing 60 mg of CS and 45 mg of SH in a gel suspension, equivalent to 1.5 c.c. of the formulation, when dealing with a large joint, and the preferred application of a mixture containing 30 mg of CS and 22.5 of SH in 0.75 cubic centimeters for a small joint. The inventor has also determined that for small joints a mixture containing 20 mg of CS and 15 mg of SH in 0.5 cubic centimeters be used every is days and on three occasions, with periodic applications every 3, 6, 9, or 12 months, depending on the results. This method produces an up to 94.5% regeneration of the articular cartilage destroyed by grade I and II osteoarthritis, according to the results obtained in the study made on 325 knees and 16 coxofemoral joints.

DETAILED DESCRIPTION OF THE COMPOUND USED IN THE TREATMENT

As mentioned previously, it is important to consider that the product is applied exactly as it is presented for intraocular use, without any changes in the formulation, using a syringe of adequate capacity with a 21×32 sterile hypodermic needle.

The used compound is 40 mg of CS and 30 mg of SH, 0.45 mg sodium monobasic monohydrate phosphate, 2.0 mg sodium dibasic anhydrous phosphate and 4.3 mg sodium chloride with injectable water, per each c.c. of viscoelastic solution.

Test Performed
Type of Studies: Prospective, Longitudinal and Experimental.

A study was conducted on 210 patients, 325 knees with chondromalacia and grades I and II osteoarthritis and 16 joints (coxofemoral) with painful articular symptoms and functional limitation, treated previously in a conventional manner with NSAIDs or with steroid infiltrations; the patients were refractory to these treatments.

Inclusion Criteria

The inclusion criteria during this study were as follows:
Patients of both sexes with chronic chondral or osteochondral pathology of the knee and coxofemoral joint up to grade II arthrosis were included, who had no clinical improvement with conventional treatment, no added autoimmune or neoplastic pathologies, of all ages, with prior arthroscopic surgery, without recent management with systemic or articular steroids or non steroid antiinflammatories (NSAIDs).

Exclusion Criteria

The following exclusion criteria were adopted: patients with grade III or upper gonarthrosis or coxarthrosis, recent or current treatment with systemic or intraarticular steroids, severe deformities and autoimmune or neoplastic pathology.

Non-Inclusion Criteria

Dropping out of treatment, death, change of medical therapy.

The Clinical Assessment was as Follows:
Pain: slight, moderate or severe.
Gait: occasional claudication, assistance of walking stick or crutches or impossibility to walk.
Mobility: complete arches, slight, moderate or severe limitation.
Synovial effusion: minimum, moderate or severe (occasional or constant). (SCRIPPS SCALE FOR SPECIAL SURGERY).

Radiographic Assessment:
Radiographic changes, articular clamping, chondromalacia and osteoarthritis. Pre- and posttreatment radiographic studies.

Arthroscopic Assessment:
Pre- and posttreatment images.

Results
210 patients were treated: 325 knees (115 bilateral (230 knees) and 95 unilateral (95 knees), 144 women (68.5%), 66 men (31.5%), aged 12 to 86 years, a mean of 44.2 years, 48 knees were diagnosed with chondromalacia, 40 with grade I osteoarthritis and 237 with grade II osteoarthritis.

Another 16 patients treated: 14 coxofemoral (hip) joints (87.5%) showed excellent results, and two coxofemoral joints (12.5%) did not report any improvement.

A visual analog clinical scale (SCRIPPS CLINIC FOR SPECIAL SURGERY) was applied and 309 knees (95.07%) showed immediate significant improvement and satisfactory evolution for up to two years of follow-up, 250 knees (83.3%) remained in the same good conditions without needing to take any NSAID for up to 50 months of follow up, 32 knees (13%) showed moderate pain and 18 cases (6%) showed no short and medium term improvement. Finally, from 16 grades I, II, III and IV osteoarthritis coxofemoral joints (hip), 14 grade I and II coxofemoral joints showed excellent results, and 2 of these grade III and IV coxotemoral joints, due to the advanced degree of deterioration, did not obtain any positive results.

None of the patients had any systemic reactions during this treatment; only one patient reported pain and a discreet increase of volume after the implantation.

Figure 8:
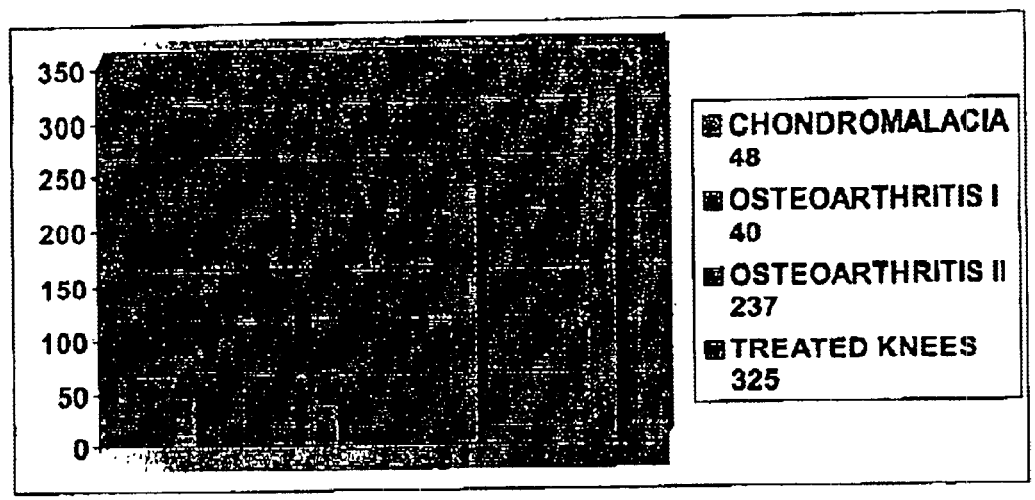
Figure 9:
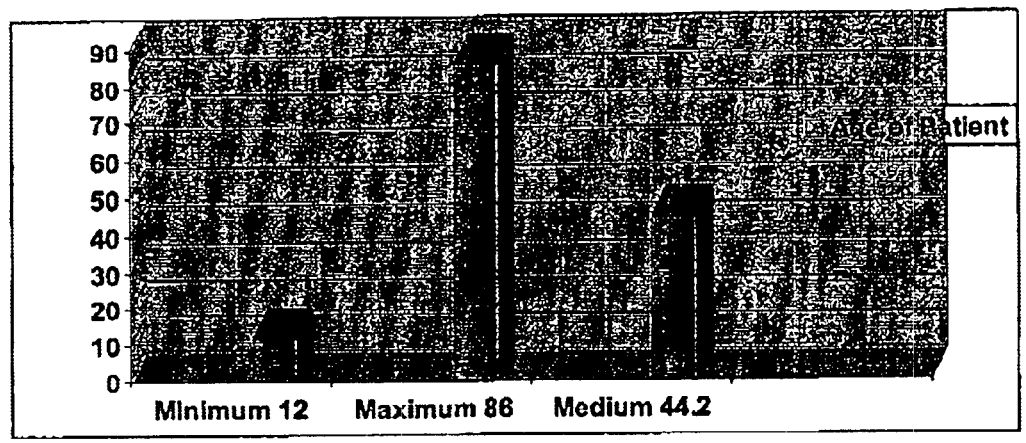
Figure 10:
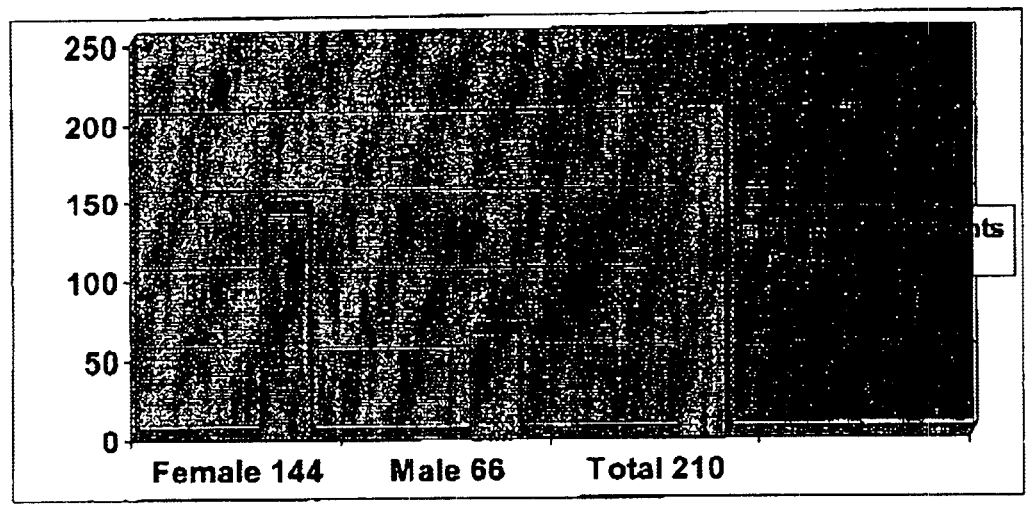

FIGS. 8–10 show the previously described results.

Figure 11:
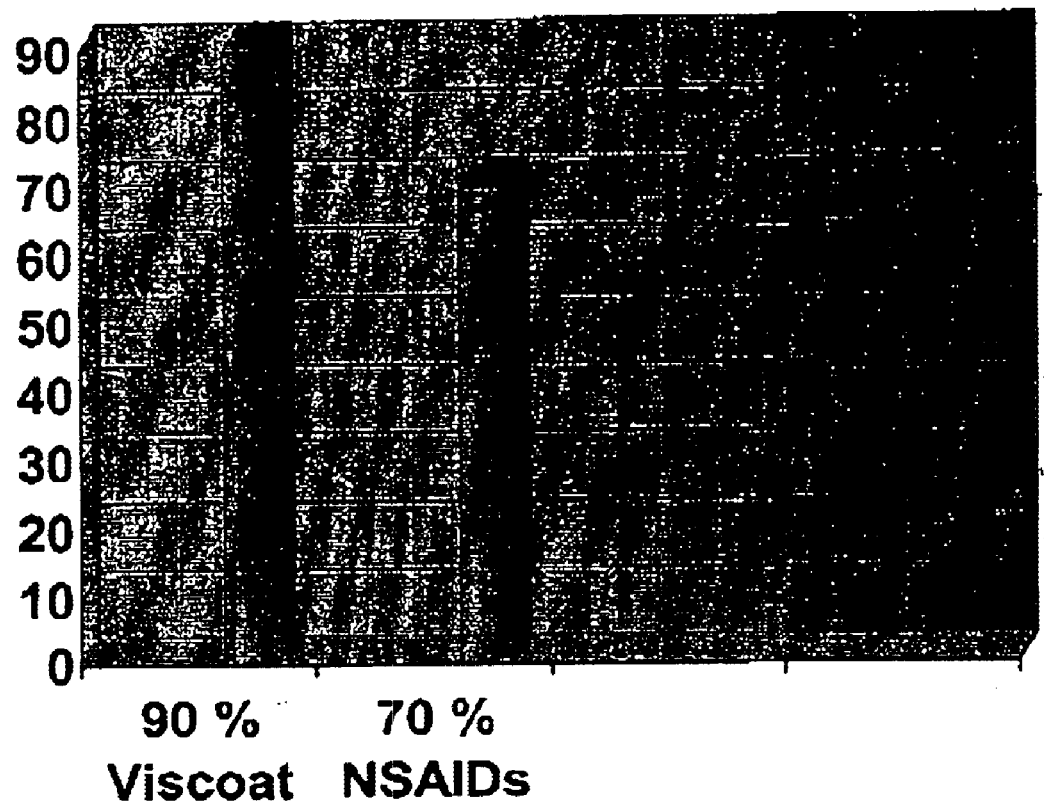
Figure 12:
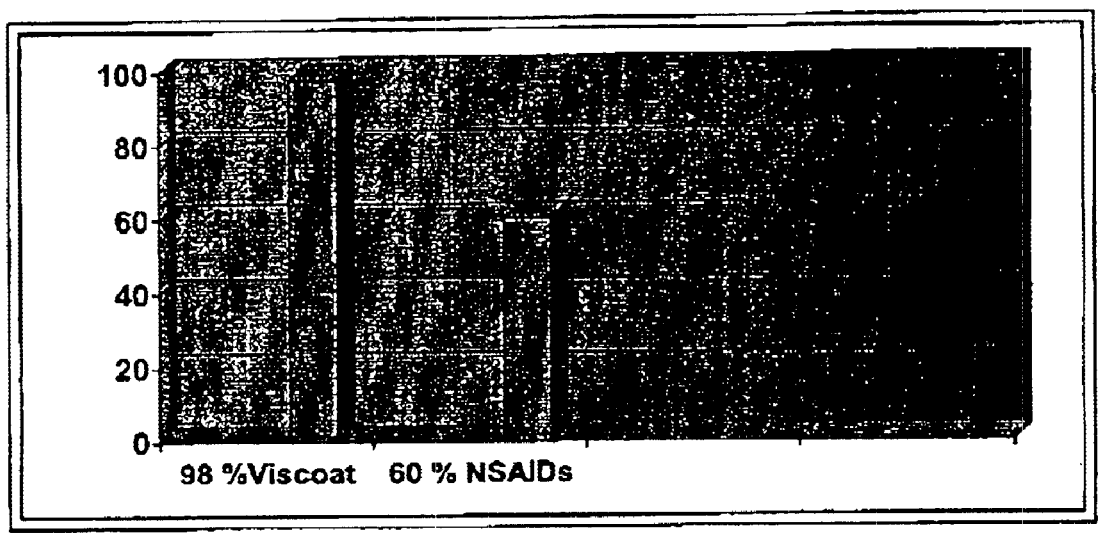

To complement the previous results, a comparative study was conducted on 20 patients treated with NSAIDs due to grade II knee osteoarthritis and 20 patients treated with Viscoat for the same reason. The results, after 90 days, were as shown in FIGS. 11 and 12. FIG. 11 shows the results for pain reduction and FIG. 12 the results for increased mobility, each after 90 days.

Figure 13:
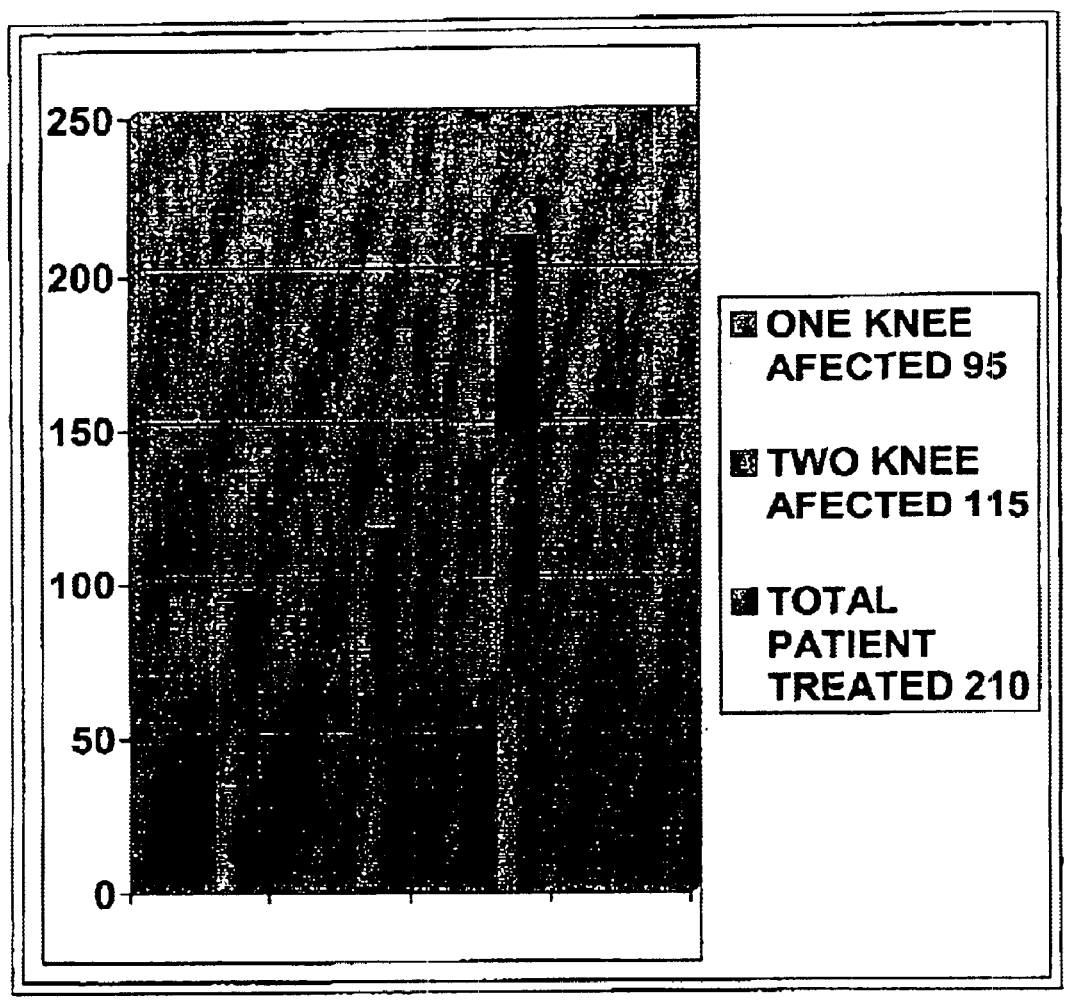
Figure 14:
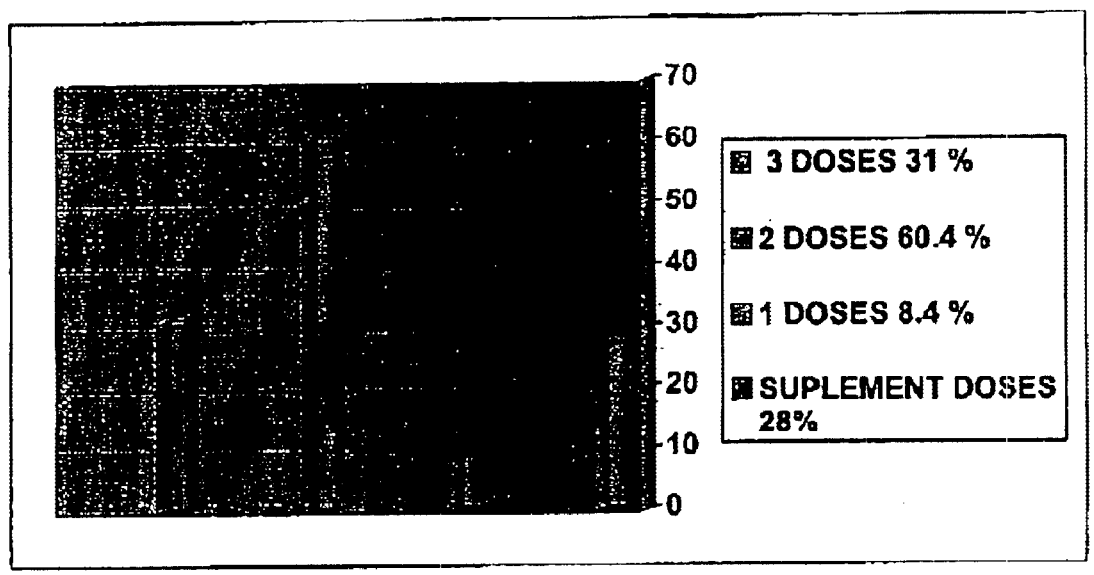

FIG. 13 shows the results after 24 months according to the HSS scale (Scripps Clinics):

Doses Applied
The study continued, as shown in FIG. 14, with the application of 3 doses of the drug to 78 knees, which represented 31% of the knees treated; 151 knees received 2 doses which represented 60.4% and 21 knees received only one dose which represented 8.4%. The 28% shown in the graph of FIG. 14 corresponds to 70 patients who, after 6 months, needed up to 8 supplementary doses; this has reduced the index of nocturnal pain, gait pain and pain at rest, and increased the range of mobility.

Figure 15:
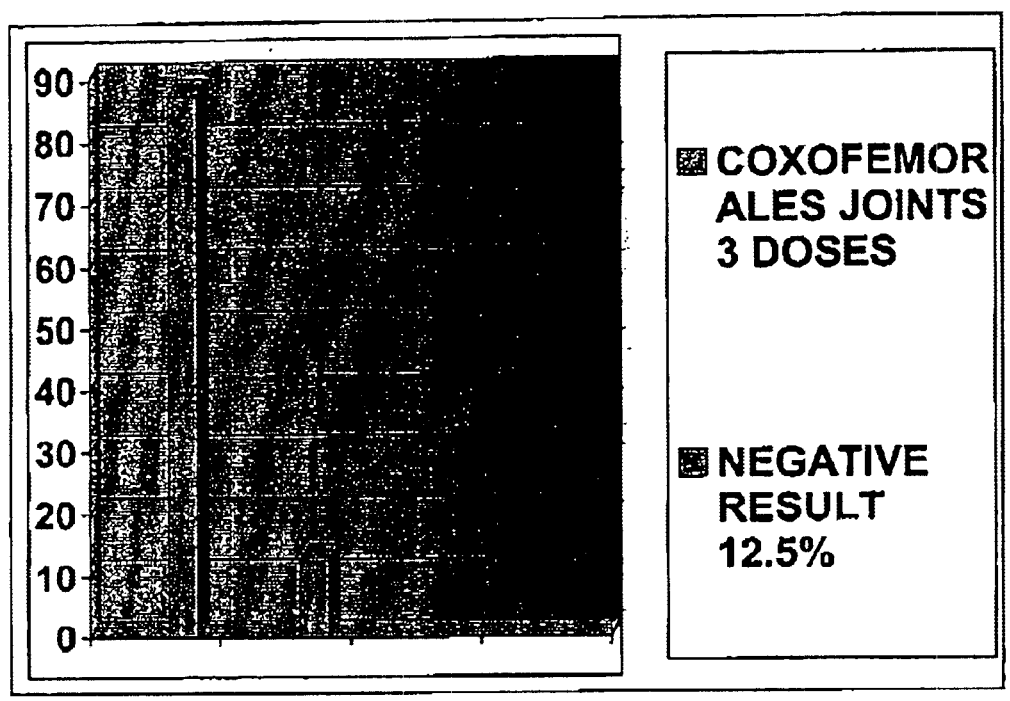

Doses Applied
FIG. 15 shows the graphic results of 16 coxofemoral joints, 3 doses covered 87.5% with excellent results in 14 coxofemoral joints treated with the drug, and the 12.5% shown in the graph of FIG. 15 corresponds to the 2 patients who did not report any positive results.

These applications were made in 9 male and 7 female patients aged 27 to 79 years.

Studies and Tests Performed on Patients that Prove Cartilage Ration by the Application of the Compound That contains CS and SH.

The following examples are given to illustrate and demonstrate the new use of the compound subject of this invention.

69 year old female patient treated previously with the compound of sodium hyaluronate and chondroitin sulfate. Biopsy of knee cartilage.

Microscopic Description:

A histological study of knee cartilage was performed. Its microscopic description was as follows: the sections present fragments of mature cartilage with islands of chondrocyte arranged regularly in groups of 2 to 3, with cohesiveness, and surrounded by a hyaline matrix without laminar fibrosis. The chondrocytes have a round nucleus, clear cytoplasm, and they are morphologically normal and with good maturation. There is no endochondral ossification or dystrophic calcification and, as in the previous example, there is no evidence of malignant neoplasia.

Diagnosis: Biopsy of knee cartilage.

De Novo cartilage formation, morphologically and architecturally normal.

Figure 3:
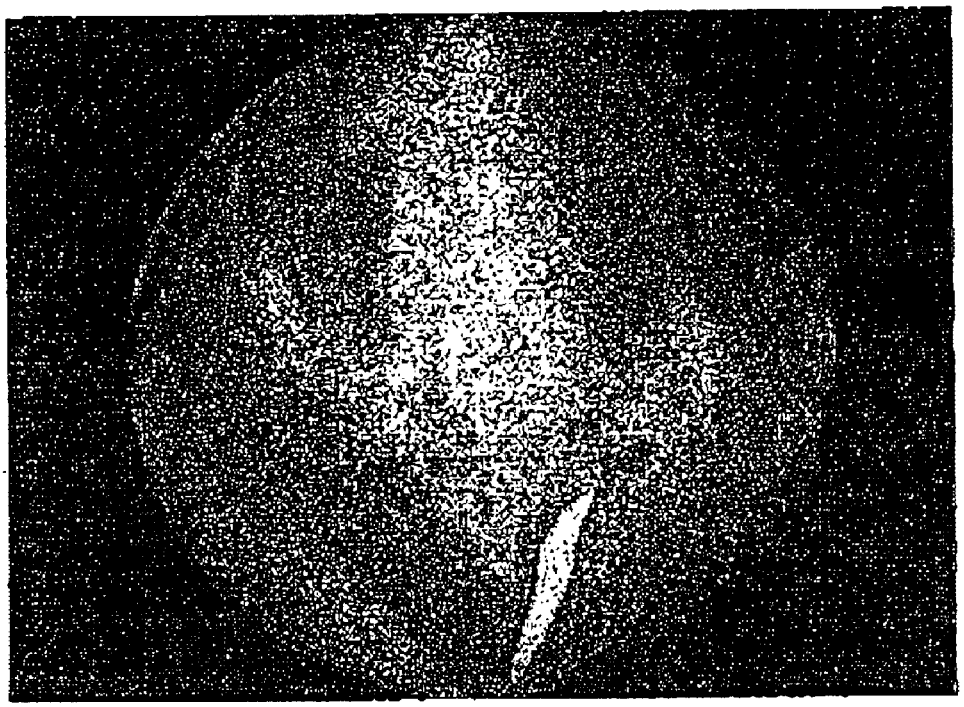

This is confirmed by the image in FIG. 3.

78-year old female patient treated previously with the compound of sodium hyaluronate and chondroitin sulfate. Biopsy of the femoral condylar cartilage.

Microscopic description:

A histologic study was made of several irregular tissue fragments that jointly measured 0.5 cm; they had a white pearly color, a firm consistency; they were identified as right and left. Paraffin technique inclusions were made of them.

Diagnosis: biopsy of femur condylar cartilage.

Figure 4:
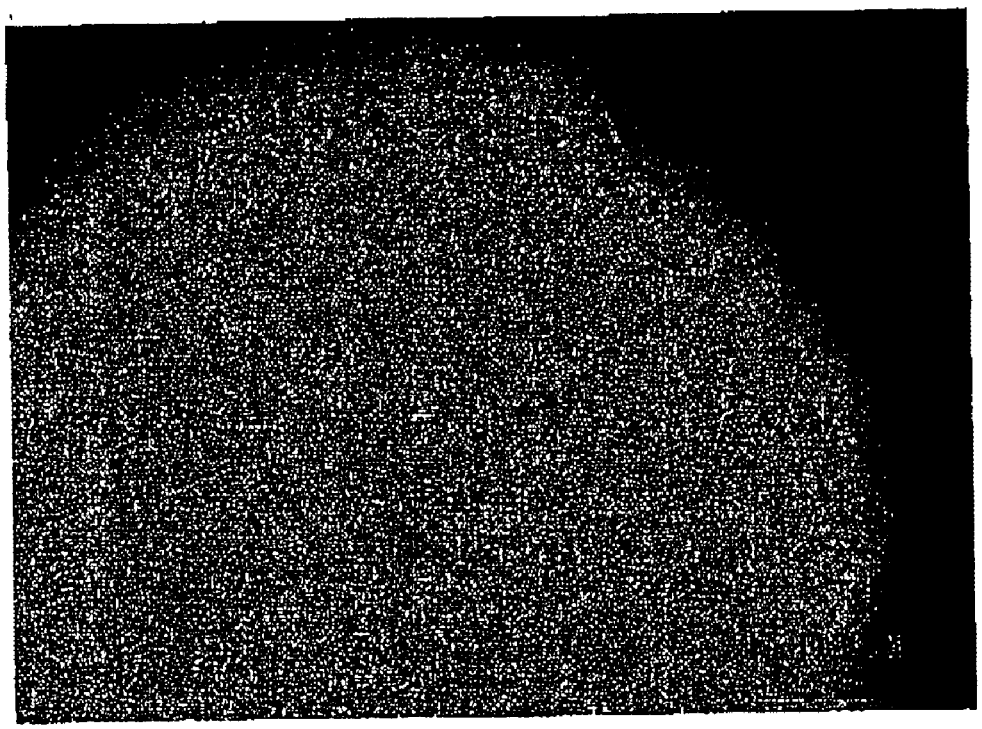
Figure 5:
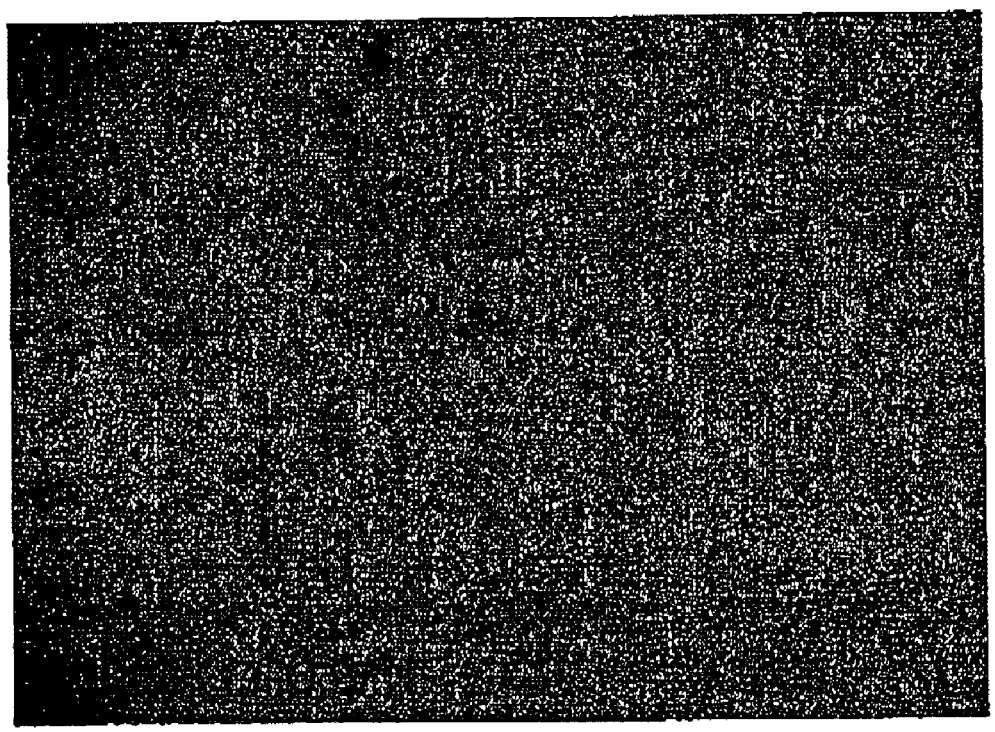
Figure 6:
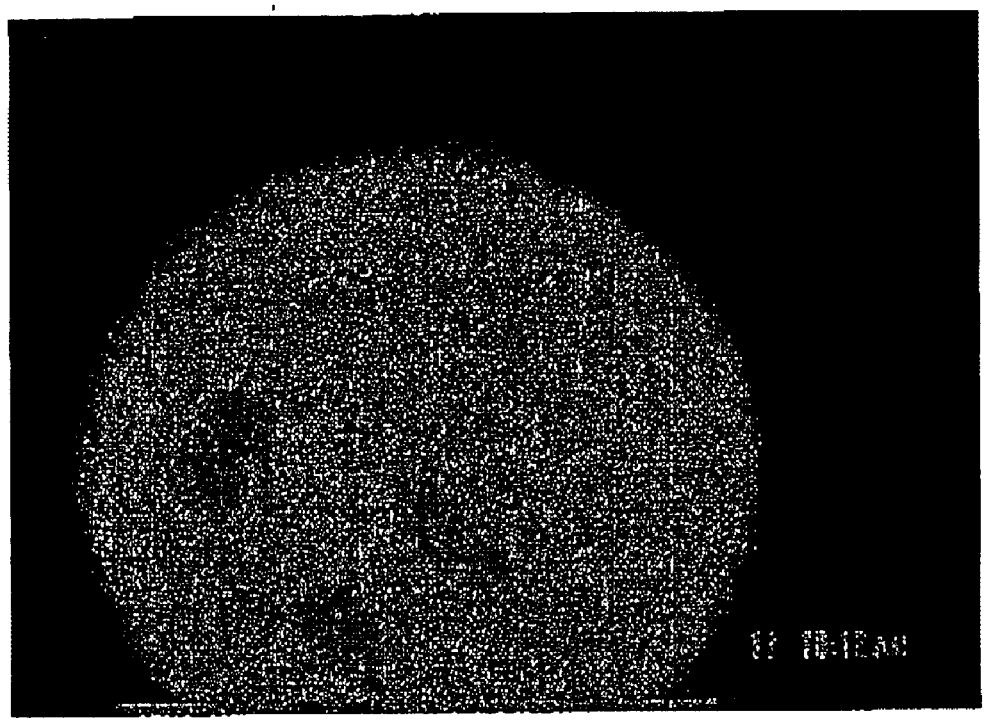
Figure 7:
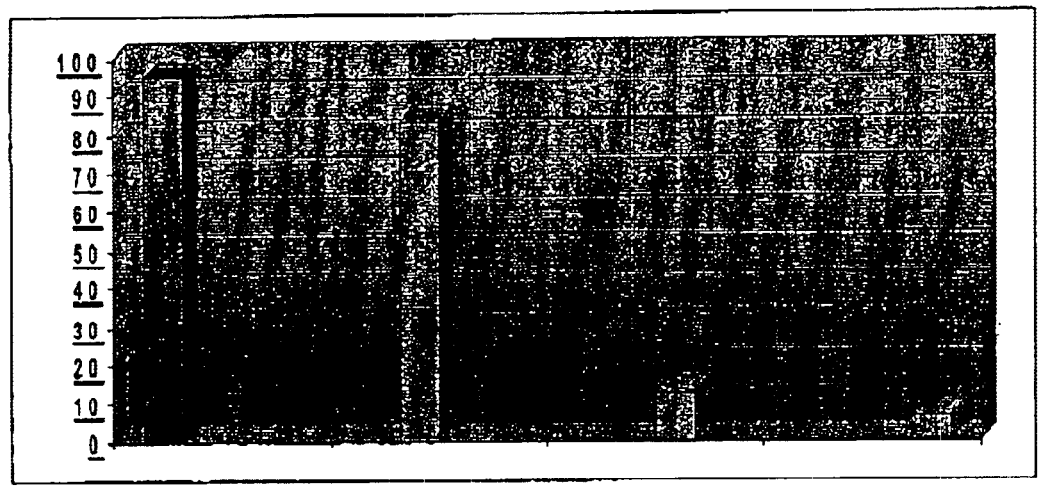
FIGS. 7 to 15 show the graphical results of the studies conducted and described herein.

Fragment of mature cartilage with partial hyalinization. (Without evidence of malignant neoplasia). See confirmation in the image of FIG. 4.

Discussion of the Results Obtained

The functional result subsequent to the implantation of the product was very satisfactory for most of treated patients. The difference between the plain systemic drug management and the intraarticular application of the chondroitin sulfate and sodium hyaluronate implant is very evidently in favor of the latter. It must be considered that the plain intraarticular rheological change (viscosity, elasticity and plasticity) reduces the pain and stimulates a synovial response, changing the viscoelastic features of the fluid. However, the basic difference lies in the medium and long term response granted by the chondrogenic induction provoked by CS and, with it, the permanent solution to the chondral lesion, 1 to the clinical manifestations and the functional disability, as well as to the risk of major surgery.

Conclusions:

The treatment of osteochondral lesions with intraarticular sodium chondroitin sulfate and sodium hyaluronate has proven to have a significantly favorable clinical response compared with the conventional treatment. This response has been confirmed with pre- and posttreatment arthroscopic imaging, conventional and electron microscope examination as well as histophysiology testing (POSITIVE S-100 Protein) showing that the damaged cartilage is regenerated in a period of about 2 years recovering its normal structure and function. The indications for the chondrogenic induction intraarticular treatment must be addressed to patients with chondromalacia and grades I and II osteoarthritis in any joint of the human body.

The original cause of the osteochondral pathology should invariably be treated, as the long-term result of the procedure will depend on that. Prior surgical management, where indicated, through minimal invasive surgery, is an excellent alternative for the integral management of osteochondral lesions and their better long-term prognosis.

Therefore, the mixture of sodium hyaluronate and sodium chondroitin sulfate can be used now in defined amounts in a therapeutically useful manner for all the characterized pathological conditions by the simple intraarticular application route, and the absence of risks of both components makes this therapy particularly attractive.

The experts in the technique will recognize that the preferred modes may be altered or amended without straying away from the true spirit and scope of the invention as defined in the enclosed claims.

What is claimed is:

1. A therapeutic method for the treatment of a mammalian joint with articular cartilage exhibiting degeneration caused by osteoarthritis, comprising (i) the intraarticular implantation of a pharmaceutically effective amount of a viscoelastic composition comprising an aqueous vehicle with 40 mg of chondroitin sulfate and 30 mg of sodium hyaluronate per cubic centimeter of said vehicle.

2. The therapeutic method according to claim 1, wherein the mammalian joint is a human joint, the intraarticular implantation is effected with a hypodermic needle, and the articular cartilage is selected from the group consisting of the following joints: i) knees, shoulders and sacroiliac; ii) coxofemoral, ankles and elbows; and iii) interphalangeal and wrists.

3. The therapeutic method according to claim 1, in which the pharmaceutically effective amount comprises 1.5 cubic centimeters of the composition according to claim 1 for a joint selected from the group consisting of: knee, shoulder and sacroiliac.

4. The therapeutic method according to claim 1, in which the pharmaceutically effective amount comprises 0.75 cubic centimeters of the composition according to claim 1 for a joint selected from the group consisting of: coxofemoral, ankle and elbow.

5. The therapeutic method according to claim 1, in which the Pharmaceutically effective amount comprises 0.5 cubic centimeters of the compound according to claim 1 for a joint selected from the group consisting of interphalangeal and wrist.

* * * * *